(12) United States Patent
Eshetu et al.

(10) Patent No.: US 10,183,797 B2
(45) Date of Patent: Jan. 22, 2019

(54) TRACE DETECTION MEDIA CARTRIDGES AND KITS

(75) Inventors: Abiy Eshetu, Arlington, MA (US); David J. Rutter, North Andover, MA (US)

(73) Assignee: DSA DETECTION LLC, North Andover, MA (US)

( * ) Notice: Subject to any disclaimer, the term of this patent is extended or adjusted under 35 U.S.C. 154(b) by 1098 days.

(21) Appl. No.: 13/546,302

(22) Filed: Jul. 11, 2012

(65) Prior Publication Data

US 2014/0014537 A1    Jan. 16, 2014

(51) Int. Cl.
  *B65D 75/00*   (2006.01)
  *B65D 77/04*   (2006.01)
  *G01N 1/02*    (2006.01)

(52) U.S. Cl.
  CPC ... *B65D 77/0453* (2013.01); *G01N 2001/022* (2013.01); *G01N 2001/028* (2013.01); *Y10T 29/49* (2015.01)

(58) Field of Classification Search
  USPC .................................. 206/569, 216; 422/430
  See application file for complete search history.

(56) References Cited

U.S. PATENT DOCUMENTS

| | | | | |
|---|---|---|---|---|
| 5,143,210 | A * | 9/1992 | Warwick et al. | 206/738 |
| 5,505,308 | A * | 4/1996 | Eikmeier et al. | 206/449 |
| 5,806,678 | A | 9/1998 | Håkansson | |
| 5,833,057 | A * | 11/1998 | Char et al. | 206/204 |
| 6,497,845 | B1 * | 12/2002 | Sacherer | 422/561 |
| 6,569,676 | B1 * | 5/2003 | Tripp et al. | 435/307.1 |
| 8,394,343 | B2 * | 3/2013 | Chan et al. | 422/555 |
| 2003/0042170 | A1 * | 3/2003 | Bolanos | 206/570 |
| 2007/0289894 | A1 * | 12/2007 | Tennant et al. | 206/569 |
| 2008/0073242 | A1 * | 3/2008 | Hein et al. | 206/569 |
| 2008/0287829 | A1 * | 11/2008 | Moore et al. | 600/573 |
| 2008/0289991 | A1 * | 11/2008 | Sgarabottolo | 206/569 |
| 2009/0134056 | A1 * | 5/2009 | Burns | 206/569 |
| 2009/0291449 | A1 * | 11/2009 | Knapp et al. | 435/6 |
| 2012/0228189 | A1 * | 9/2012 | Alhajri | 206/569 |

FOREIGN PATENT DOCUMENTS

| | | |
|---|---|---|
| EP | 0393734 A1 | 10/1990 |
| EP | 0586125 A2 | 3/1994 |
| KR | 20090025713 A | 3/2009 |

OTHER PUBLICATIONS

Notification of Transmittal of the International Search Report and the Written Opinion of the International Searching Authority dated Dec. 20, 2013 for International Application No. PCT/US2013/049901.
Notification of Transmittal of the International Preliminary Report on Patentability and the Written Opinion of the International Searching Authority dated Jan. 22, 2015 for International Application No. PCT/US2013/049901.
International Preliminary Report on Patentability and Written Opinion of the International Searching Authority dated Jan. 13, 2015 for International Application No. PCT/US2013/049901.

* cited by examiner

*Primary Examiner* — Jacob K Ackun
(74) *Attorney, Agent, or Firm* — Lando & Anastasi, LLP

(57) ABSTRACT

Trace detection media cartridges and kits to facilitate trace detection of contraband. A cartridge may store consumables to prevent contamination and may also aid in the dispensing of consumables. A housing may hold a consumables cartridge and further prevent spoilage, such as with a self-closing lid. A trace detection kit may include a housing and at least one cartridge storing consumables.

6 Claims, 8 Drawing Sheets

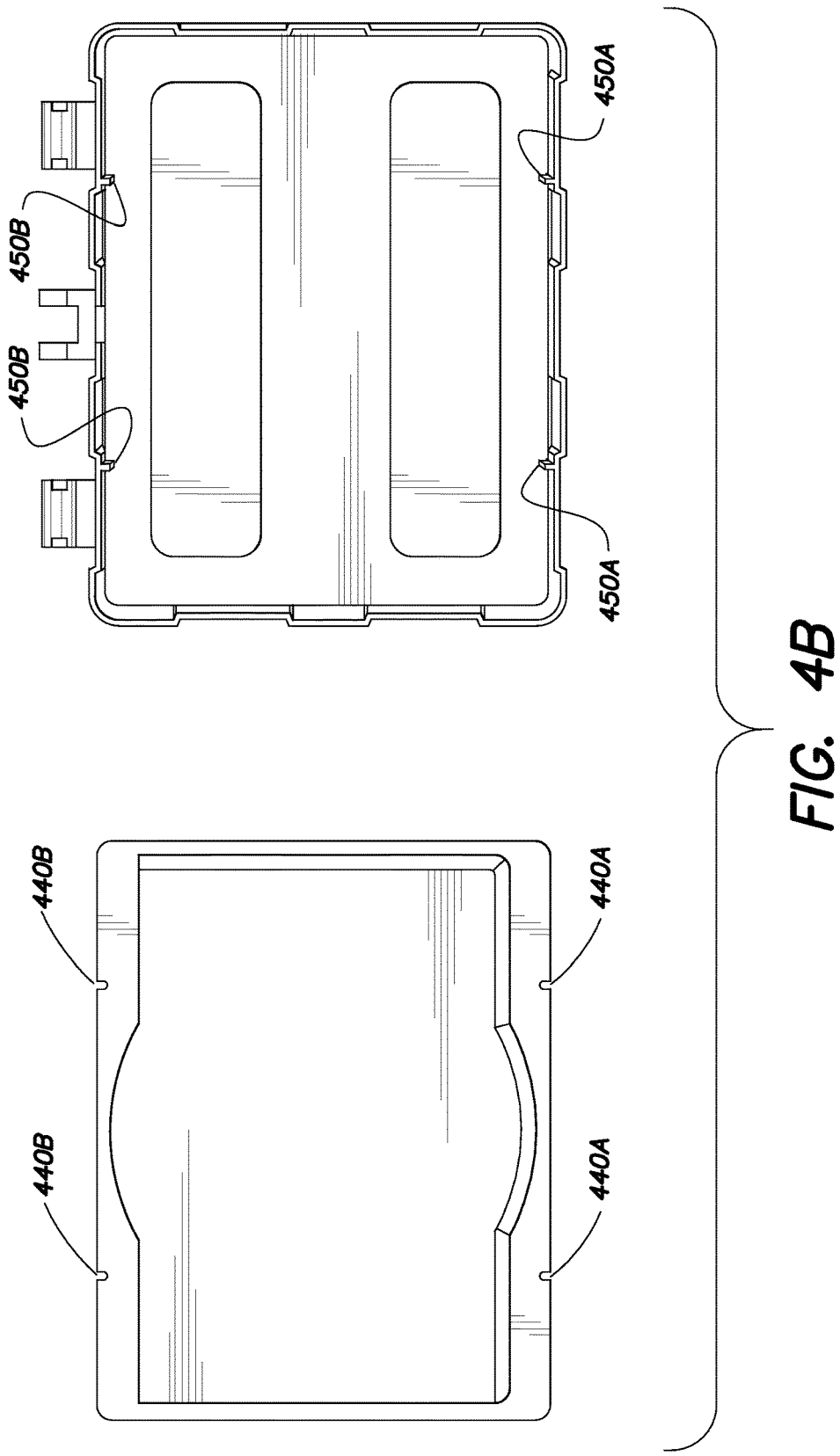

TRACE DETECTION MEDIA CARTRIDGES AND KITS

FIELD OF THE TECHNOLOGY

One or more aspects relate generally to the trace detection of contraband, such as illicit narcotics and/or explosives and, more particularly, to trace detection media cartridges and kits to facilitate sample collection for testing or verification of trace detection instruments.

BACKGROUND

Contraband detection is an essential element of many security programs. It is imperative that contraband, including narcotics and explosives, be identified and contained before it is trafficked or otherwise used for unlawful purposes such as terrorism. Contraband detection is crucial for homeland security, particularly in the transportation sector. For example, the Transportation Security Administration (TSA) has mandated the use of explosives and narcotics trace detection (ETD) equipment to screen passengers and baggage as part of an approved security program. Contraband detection techniques generally involve sample collection and the subsequent analysis thereof.

SUMMARY

Aspects and embodiments of the present invention relate to trace detection media containers and facilitate contraband trace detection. Trace detection media, known as trace detection consumables, or simply consumables, may be used to collect trace chemical samples from objects and for testing the collected samples for the presence of substances such as explosives and/or illicit drugs. Consumables may also be used to calibrate trace detection/analysis systems and/or verify that such systems are working properly. Consumables are known to degrade, spoil, and become contaminated during trace detection, which presents an obstacle to efficient contraband detection activities.

In accordance with an aspect of the present invention there is provided a consumables kit comprising a cartridge configured to receive trace detection consumables. The cartridge contains at least one trace detection consumable. The kit further comprises a cartridge housing constructed and arranged to receive the cartridge.

In accordance with some embodiments, the housing comprises a self closing lid.

In accordance with some embodiments, the self-closing lid comprises a gasket configured to promote a substantially air-tight seal.

In accordance with some embodiments, the housing comprises a shelf configured to hold dispensed-consumables.

In accordance with some embodiments, the housing includes a mount configured to removably secure the housing to an external surface.

In accordance with some embodiments, the cartridge comprises a protective barrier configured to prevent contamination, spoilage, or degradation of the plurality of trace detection consumables.

In accordance with some embodiments, the kit further comprises a dispenser configured to facilitate use of the trace detection consumables by an operator.

In accordance with some embodiments, the dispenser comprises a re-sealable cover.

In accordance with some embodiments, the kit comprises first and second trace detection consumables within the cartridge, wherein the first trace detection consumable is different than the second trace detection consumable.

In accordance with some embodiments, the kit comprises a second consumables cartridge.

In accordance with some embodiments, the kit comprises indicia to facilitate differentiation between the first and second trace detection consumables by an operator.

In accordance with an aspect of the present invention there is provided a consumables cartridge comprising a container constructed and arranged to receive a plurality of trace detection consumables and a dispenser to facilitate access to the trace detection consumables.

In accordance with some embodiments, the container comprises a barrier configured to prevent contamination, spoilage, or degradation of the trace detection consumables.

In accordance with some embodiments, the container is configured to receive different types of trace detection consumables.

In accordance with some embodiments, the cartridge further comprises a coding system configured to facilitate identification of the trace detection consumables.

In accordance with some embodiments, the shape of the container is configured to mate with a corresponding shape of a cartridge housing.

In accordance with some embodiments, the container is configured to nest with a second cartridge.

In accordance with an aspect of the present invention, a method of facilitating contraband detection is provided comprising providing a trace detection consumables cartridge including a plurality of trace detection consumables and providing instructions to insert the consumables cartridge into a consumables cartridge housing.

In accordance with some embodiments, the method comprises providing the consumables cartridge housing.

In accordance with some embodiments, the method comprises providing instructions for dispensing the trace detection consumables.

Still other aspects, embodiments, and advantages of these exemplary aspects and embodiments are discussed in detail below. Embodiments disclosed herein may be combined with other embodiments in any manner consistent with at least one of the principles disclosed herein, and references to "an embodiment," "some embodiments," "an alternate embodiment," "various embodiments," "one embodiment" or the like are not necessarily mutually exclusive and are intended to indicate that a particular feature, structure, or characteristic described may be included in at least one embodiment. The appearances of such terms herein are not necessarily all referring to the same embodiment.

BRIEF DESCRIPTION OF THE DRAWINGS

Various aspects of at least one embodiment are discussed below with reference to the accompanying figures, which are not intended to be drawn to scale. The figures are included to provide illustration and a further understanding of the various aspects and embodiments, and are incorporated in and constitute a part of this specification, but are not intended as a definition of the limits of the invention. Where technical features in the figures, detailed description or any claim are followed by reference signs, the reference signs have been included for the sole purpose of increasing the intelligibility of the figures and description. In the figures, each identical or nearly identical component that is illustrated in various figures is represented by a like numeral. For purposes of clarity, not every component may be labeled in every figure. In the figures:

FIG. 4B presents a top view of components of an unassembled kit in accordance with one or more embodiments.

DETAILED DESCRIPTION

Figure 1B:
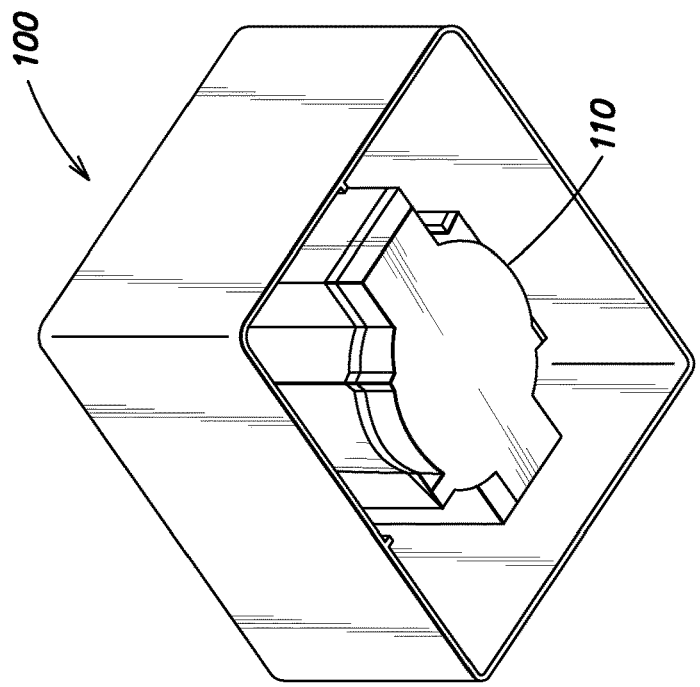
FIG. 1B presents a bottom perspective view of a cartridge in accordance with one or more embodiments.

One or more embodiments relate generally to contraband trace detection. In trace detection, it is critical that samples be accurately collected and analyzed. It is therefore essential that trace detection media remains free of contaminants. Additionally, trace detection media may spoil over time and precautions must be taken to ensure that detection media remains viable. Contaminated and/or spoiled media presents an obstacle to the detection of contraband. One or more embodiments may confer particular advantages over conventional trace detection methods and products. Some embodiments may involve a trace detection kit that helps ensure that sample media does not become contaminated or spoiled. Other embodiments may involve a sample media cartridge that provides particular advantages over conventional media containers. Such a cartridge may advantageously cooperate with a trace detection kit to facilitate dispensing of consumables for sample collection. The embodiments disclosed herein may augment the effectiveness of contraband trace detection by improving the ease with which an operator may obtain a sample and by ensuring the efficacy of such samples. Thus, one or more embodiments may enhance trace detection capabilities, leading to an overall improvement in various security operations.

The collection of trace samples from objects to test for the presence of contraband, such as explosives or illicit drugs, has become a concern in recent years, especially in environments such as airports or other transportation hubs. It is believed that the testing of suspect packages or other objects for the presence of contraband may serve to deter the trafficking of drugs and/or explosives, as well as their use for unlawful purposes such as terrorism.

Contraband may include, for example, explosives, narcotics, or any other substance of concern. Contraband detection may involve any method for detecting trace amounts of contraband. In at least some trace detection techniques, test samples are collected on swabs of trace detection media. Samples may be in the form of solids, liquids, gels or gases. In some embodiments, once a sample has been collected, it may be transferred to an analysis/detection system to test for the presence of contraband. Appropriate test systems may include, for example, gas chromatographs, mass spectrometers, Fourier transform infrared spectrometers, ion trap mobility spectrometers, ion mobility spectrometers, and other systems known in the art for the analysis and identification of trace samples of materials. In some instances, the testing system may heat the sample to vaporize contraband particles and/or liquids which may be present and analysis may then be performed upon the vapor. There are many commercially available trace detectors, such as instruments available from Smiths Detection and Morpho Detection (Safran Morpho) to detect various types of contraband. In other methods, a chemical solution which reacts by, for example, changing color in the presence of a particular compound of interest may be used to test for the presence of that compound on a swab. The chemical solution may be added to a swab prior to sampling an object with the swab, or may be applied to a swab after a sample has been collected on the swab.

Contraband detection may therefore use trace detection media. Trace detection media may be recognized or known in the art as consumables, swabs, sample traps or by other terminology, all of which may be used interchangeably herein. Consumables may include any trace detection media capable of use with a trace detection device to provide detection of trapped traces of contraband. Consumables may be capable of trapping and facilitating detection of explosives, narcotics, or other substances. Consumables may further be capable of detecting more than one type of contraband. For collecting a sample, a swab or consumable may be mounted on a hand held testing wand to facilitate sampling of a suspect object by an operator. Testing wands may expose a portion of a swab for contact with a suspect object while retaining the swab by securing another portion of the swab to a portion of the testing wand. Some embodiments of testing wands may include a vacuum system configured to draw vapor through the swab. In other methods, a swab may be wiped across a surface of an object of interest by hand without the use of a testing wand.

Consumables may be formed from a sheet of substrate material. The substrate material may be, for example, paper, a fabric such as cotton or polyester, a polymer such as polyimide, polyamide, or polytetrafluoroethylene, or in some examples, a screen or mesh of fiberglass, or of a metal such as stainless steel. In some trace detection methods, a sample is transferred from a surface of an object of interest onto a consumable by wiping the swab over a portion of the surface of the object. In other methods, a vapor emanating from an object of interest, and/or air that is blown across a surface of the object is directed onto a consumable where particulates and/or vapors may be trapped. In some methods, a vacuum generator is utilized to pull gas containing vapors and/or suspended particulates from the object of interest into the consumable. In instances where it is desired to collect samples by passing potentially contaminated air through the consumable, the consumable may be sufficiently porous to provide for passage of air through the consumable yet sufficiently thick to collect a desired amount of sample material to test.

Consumables may be impregnated with one or more materials, for example, activated carbon, which may enhance the ability of the consumable to collect materials of interest. Consumables may be used for sampling or for calibration or verification. Consumables for sampling may include various components which may depend on the type of contraband to be detected. Other consumables may include trace detection media pre-contaminated with a known concentration of one or more substances of interest to serve in instrument verification and calibration. Such consumables may be transferred into a trace detection device to verify that the detector produces an output consistent with expected values given the known concentration of contaminants pre-loaded on the consumable. These consumables may thus be used to calibrate a trace detection device.

Consumables may vary in size and shape depending on the particular function of the consumable (e.g., a sample or a calibration consumable) and the type of contraband capable of being trapped by the consumable. They may be round, rectangular, or any other shape. Consumables may further vary based upon the specific trace detection device that will receive the consumable. Thus it is appreciated that in addition to varying in material and composition, the geometry of consumables may also vary widely. In at least some embodiments, consumables may be any type of sample trap commercially available from DSA Detection, North Andover, Mass.

Consumables may undesirably become contaminated prior to sampling. Consumables are also subject to spoilage due to over exposure to light and air. In accordance with one or more embodiments, consumables may remain in a substantially air-tight, light-controlled, temperature controlled environment. In at least some embodiments, exposure to excessive forces and manipulations that may harm the integrity of the consumable or otherwise result in their degradation may be avoided.

Figure 1A:
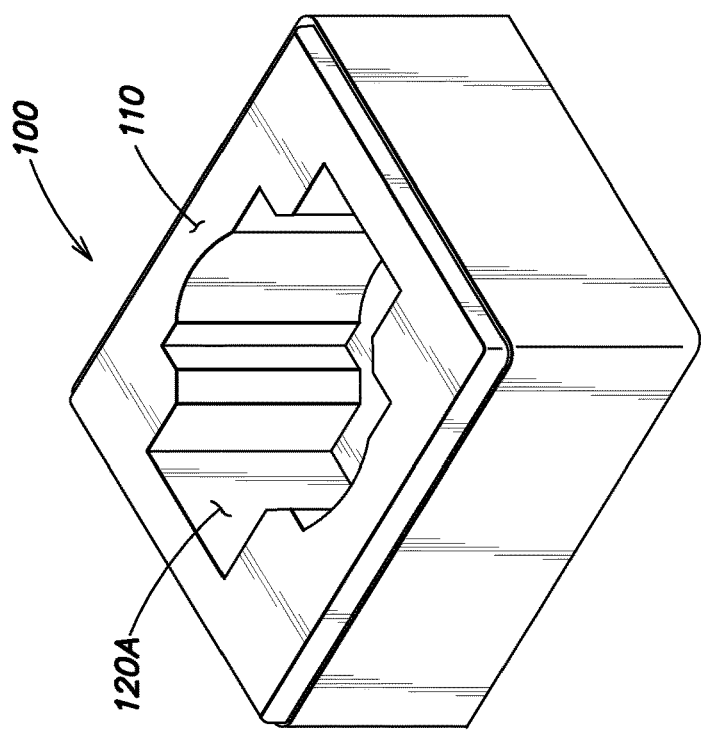
FIG. 1A presents a top perspective view of a cartridge in accordance with one or more embodiments.

One or more embodiments relate generally to a trace detection consumables cartridge that may advantageously receive, protect, and/or dispense consumables. The cartridge may be a stand-alone consumables magazine or may be a consumables insert. In accordance with one or more embodiments and referring to FIGS. 1A and 1B, a trace detection consumables cartridge 100 may include a container 110 configured to hold at least one consumable (not shown). In some embodiments, the container 110 may hold two or more consumables, such as a plurality of consumables. The container may be formed from any suitable material. Suitable materials include those that do not adversely interact with the consumables. Suitable materials further comprise materials with other desirable characteristics, including, but not limited to, materials that are environmentally friendly and/or recyclable, light weight, capable of implementing a coding system based on color or other parameter, impact resistant, durable, and cost-effective. Suitable materials may also include those capable of being thermoformed in some embodiments.

Figure 1C:
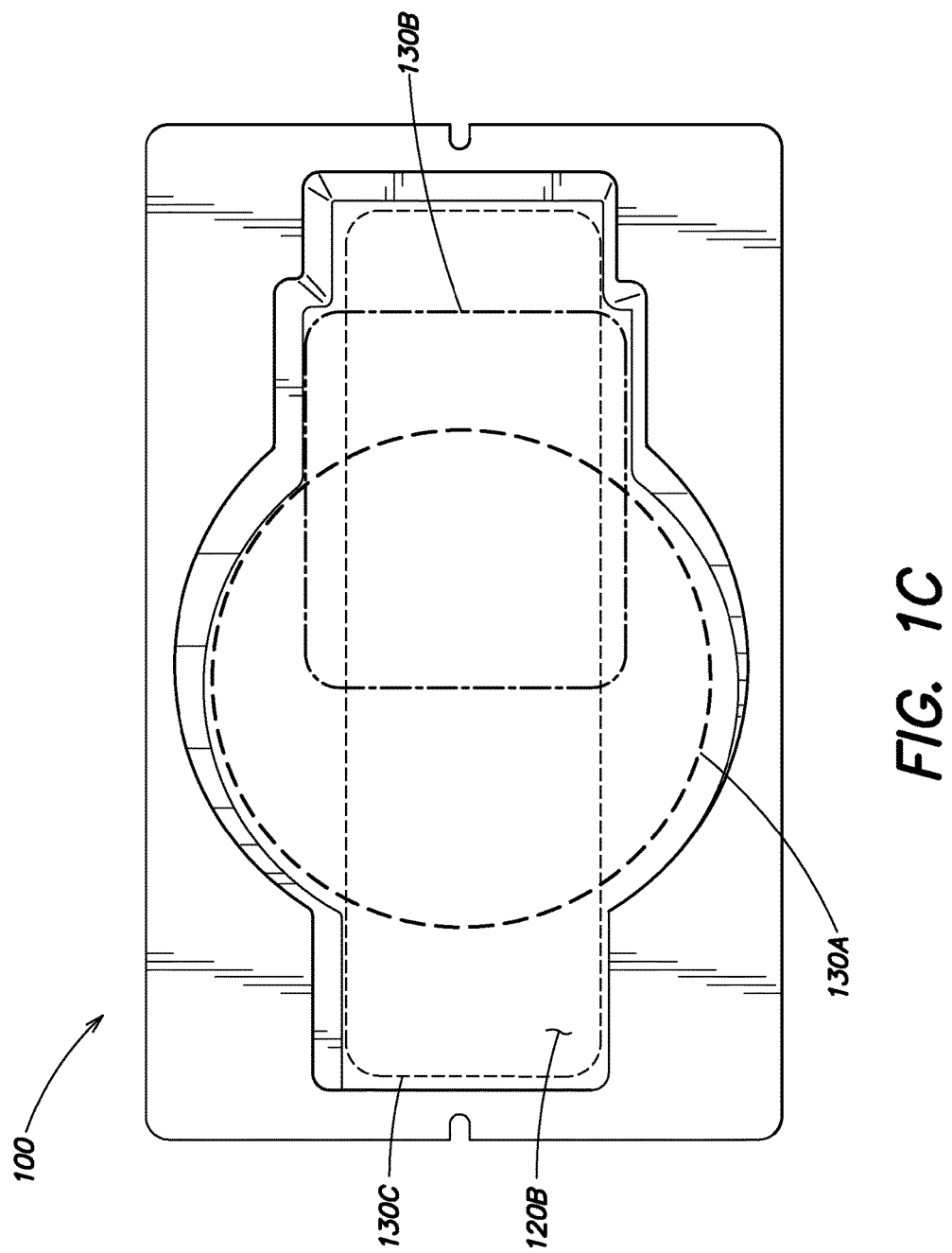
FIG. 1C presents a top view of a cartridge in accordance with one or more embodiments.

With reference to consumables cartridge 100, container 110 forms cavity 120A configured to receive consumables (not shown). In accordance with one or more embodiments, a trace consumables cartridge may advantageously be capable of accommodating one or more consumables, such as a plurality of consumables. Container 110 may define cavity 120A such that it is capable of receiving more than one type of consumable. The trace consumables cartridge may be constructed and arranged to hold consumables of different geometries or a pluralities of different consumables comprising a single geometry. Referring to FIG. 1C, consumables cartridge 100 having cavity 120B is capable of holding consumables having a plurality of geometries, as shown by dotted lines. Cavity 120B may hold consumables having geometries indicated by dotted lines 130A, 130B, or 130C. Thus a single cartridge may be capable of holding a plurality of distinct consumables in terms of one or more parameters. For example, the cartridge may be loaded with one type of consumable having a single geometry, or the cartridge may be loaded with two types of consumables having the same geometry. When loaded with two types of consumables having the same geometry, the consumables may be separated by the particular construction and arrangement of the cavity formed by the container. Alternatively, more than one type of consumable, each having varied geometry, may be capable of being loaded in a single cartridge.

In accordance with one or more embodiments of a trace detection consumables cartridge, the cartridge may prevent contamination or spoilage of the consumables. Contaminated and spoiled consumables prevent proper sample collection and present an obstacle to reliable contraband detection. In one or more embodiments, a trace consumables cartridge containing consumables may be substantially sealed by a cover, shrink wrap, or other known packing materials to prevent degradation or contamination of the consumables prior to using the cartridge to facilitate trace detection. In accordance with one or more embodiments of a trace detection consumables cartridge, the cartridge container may be constructed and arranged to form a cavity capable of receiving a plurality of consumables. The cavity may be enclosed by one or more protective layers to prevent contamination of consumables loaded within the cavity. These layers may provide additional safeguards against contamination. Protective layers may provide consumables protection when the cartridge is unwrapped from its external protective packaging. The protective layers of one or more embodiments are constructed and arranged to prevent contamination, spoilage, and/or degradation of the consumables. Protective layers may also be associated with individual consumables stored in the cartridge.

A protective layer in accordance with one or more embodiments may allow an operator to access the consumables to facilitate trace detection. The protective layer may be constructed from any suitable material and may be arranged as a flap or tuck top that protects the consumables from contamination and spoilage but also permits operator access. The protective layer may be configured to seal the cavity containing consumables and thus may reduce the likelihood of consumable contamination and/or degradation.

Figure 2B:
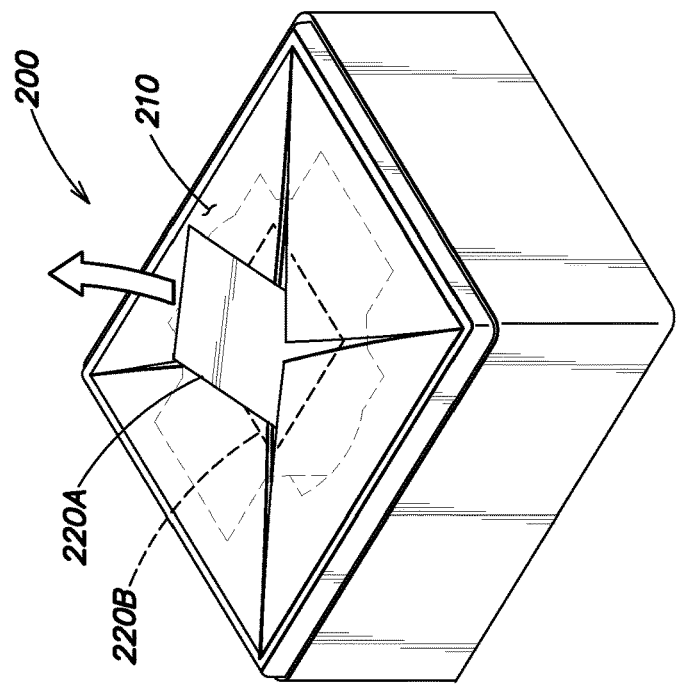
FIGS. 2A and 2B present perspective views of a cartridge with a dispensing mechanism in accordance with one or more embodiments.
Figure 2A:
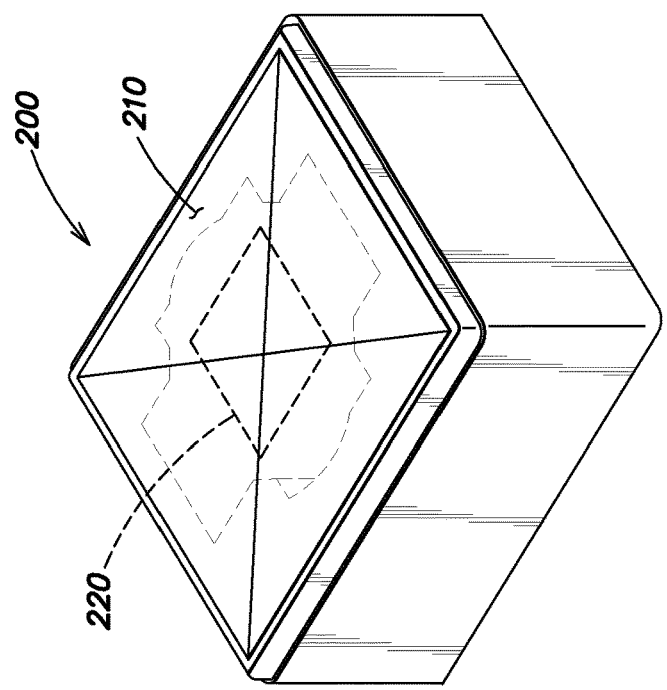

In one or more embodiments and referring to FIGS. 2A and 2B, a trace consumables cartridge 200 may be constructed and arranged to include a dispenser 210. Dispenser 210 may cooperate with consumables 220 contained in the cartridge. The dispenser may, for instance, comprise a tuck top or a slit feature that allows for the dispensing of only one consumable at a time. In some embodiments and referring to FIG. 2B, a first consumable 220A must be extracted from the dispensing feature before a second consumable may be dispensed. Consumables 220B loaded in the cartridge and not yet dispensed thus remain enclosed in the cavity of the cartridge. In other embodiments, two or more consumables may be dispensed simultaneously. The dispenser may also function as a protective barrier between the undispensed consumables and contaminants, light, and air. The dispensing feature of one or more embodiments may thus ensure that consumables do not become exposed to contaminants, light, or air, at least before they are dispensed from the dispenser.

In some embodiments, the dispenser may include a resealable cover capable of enclosing and sealing the cavity. When the dispensing feature is engaged, the cover is in the open position and allows access to the consumables contained in the cavity. According to one or more embodiments, the dispensing feature may cooperate with the cover to remove a consumable from the cavity. When an operator removes the selected consumable, the dispensing feature may automatically cause the cover to close, resealing the consumables in the cavity. The dispensing feature may thus also function as a protective barrier between the undispensed consumables and contaminants, light, and air. The dispensing feature of one or more embodiments ensures that consumables do not become exposed to contaminants, light, or air, at least before they are dispensed from the dispenser. In some embodiments, the dispenser may be integral to the lid. Still, in other embodiments, the dispenser may comprise a spring loaded element that pushes a single consumable to the surface of a cavity.

In some embodiments of a trace consumables cartridge, the cartridge may be constructed and arranged to improve shipping and storing of consumables. In one or more embodiments, a trace consumables cartridge is configured to facilitate nesting. A nesting system, such as an embedded mating system, may allow consumables cartridges to advantageously stack within one another, such that the overall space occupied by a plurality of trace consumables cartridges may be reduced. The nesting feature may comprise a container configuration that allows the protrusion of the cavity of a first cartridge to fit within the interior of the cavity formed by a second cartridge container. In one or more embodiments, the external base of the first cartridge's cavity rests within the second cartridge's cavity, such as with corresponding male and female structures. In one or more embodiments, the first and second cartridges have consumables loaded in the cavity. The consumables are sealed such that they are protected from any contaminants present on the nesting cartridge. In some embodiments, the whole cartridge, including the loaded consumables, may be sealed with a protective material. The nesting system may reduce the amount of space required to store and ship trace consumables cartridges.

Figure 4A:
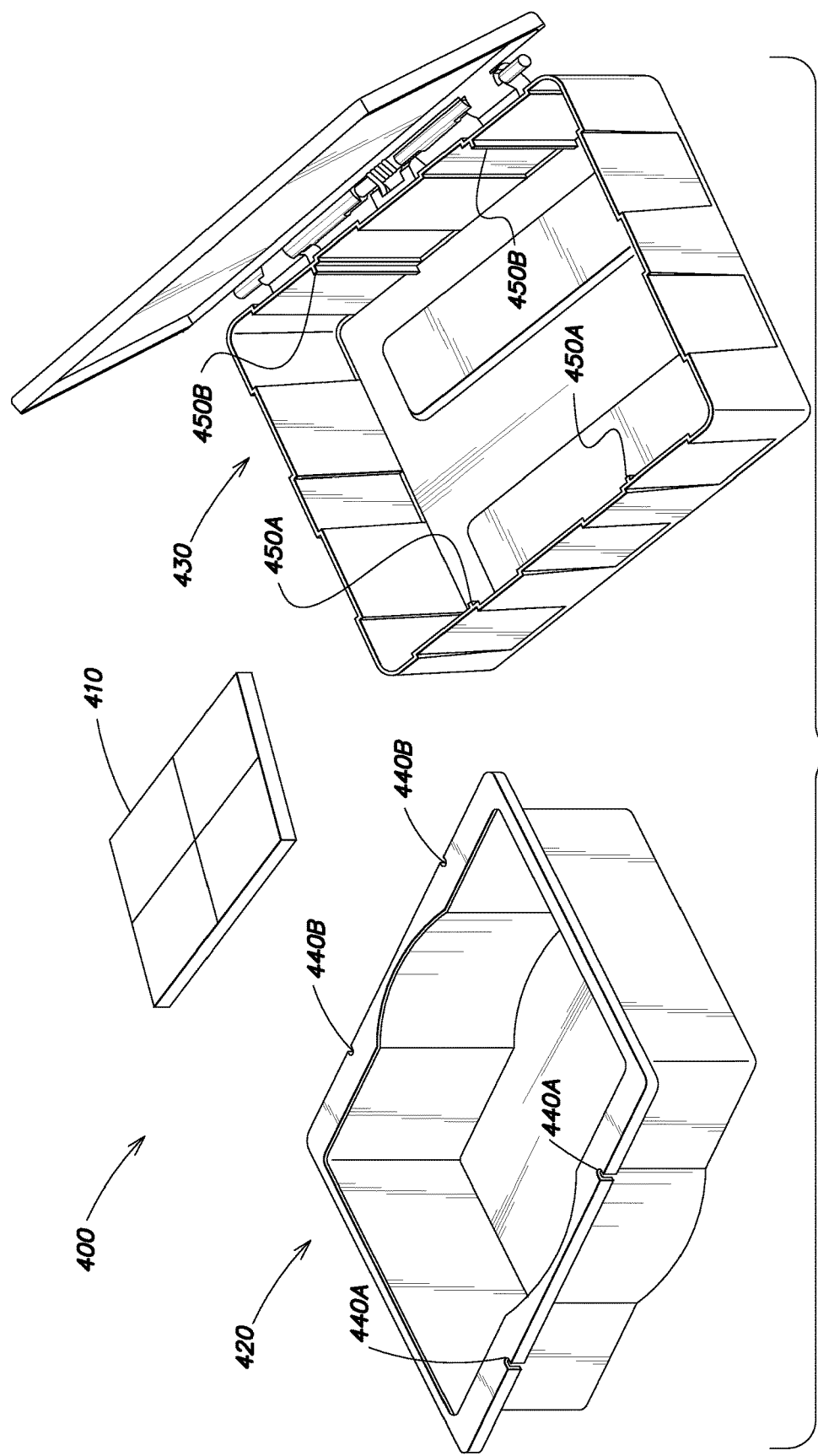
FIG. 4A presents a kit in an unassembled state in accordance with one or more embodiments.

In accordance with one or more embodiments, a trace consumables cartridge may advantageously cooperate with other contraband detection items. In some embodiments, the cartridge may engage with a sample wand to facilitate dispensing. In one or more embodiments, a trace consumables cartridge may engage or cooperate with a consumables cartridge housing. A mating system may allow the trace consumables cartridge to be removably received by a consumables cartridge housing. The feature may, for instance, comprise structural elements incorporated into the cartridge container that allow the cartridge to be received by the housing. The housing may comprise complimentary structural elements, for example male and female structures, such that the cartridge and housing can cooperate with one another. Such structures may include hole punches, for instance, such that the cartridge can fit over corresponding pegs in a housing, interlocking depressions and protrusions, or other arrangements capable of mating the cartridge to the housing. Referring to FIGS. 4A and 4B, cartridge depressions 440 cooperate with housing protrusions 450. Depressions 440A cooperate with protrusions 450A and depressions 440B cooperate with protrusions 450B to mate the cartridge with the housing. Still other complimentary structures may include features that cause the cartridge to mate with the housing in such a way that it locks into place.

Figure 3A:
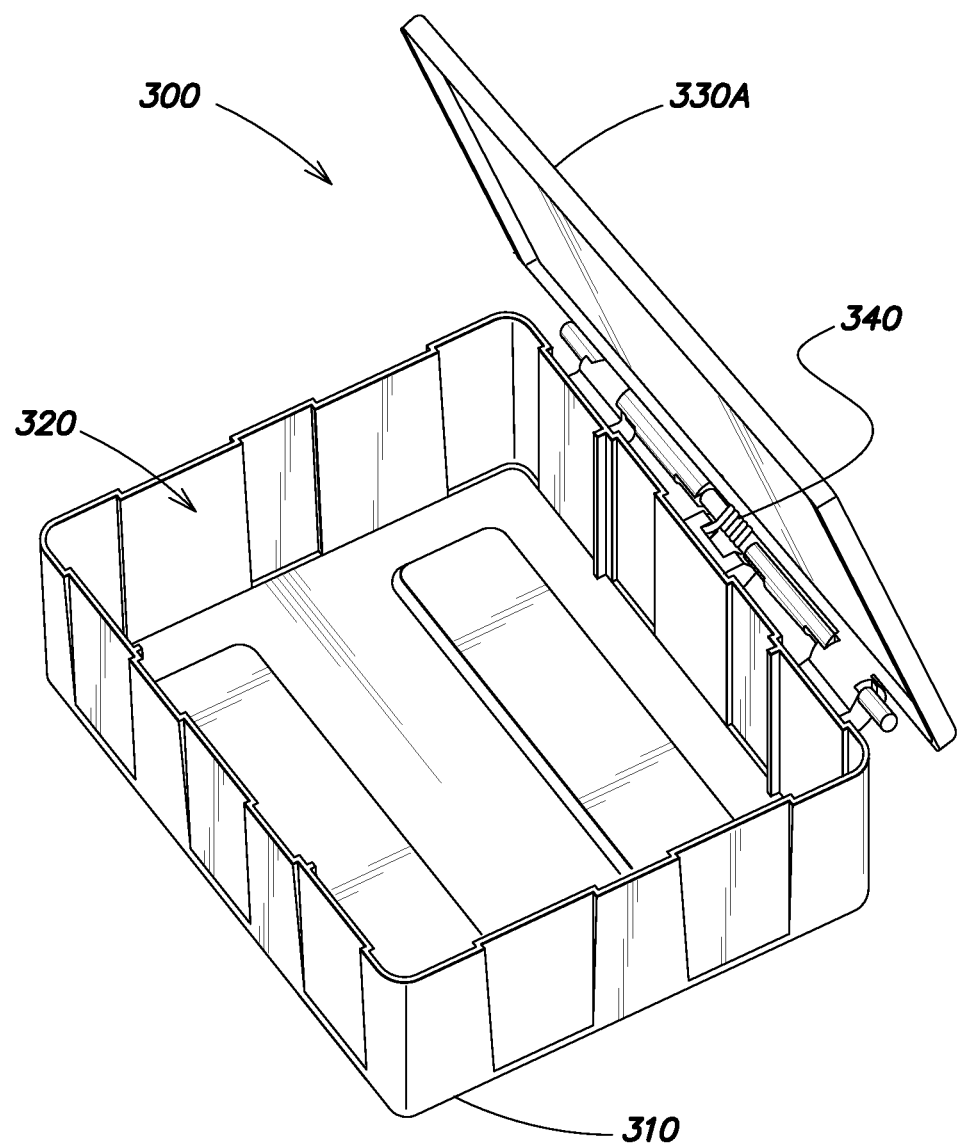
FIGS. 3A-3C present perspective views of cartridge housings in accordance with one or more embodiments.
Figure 3C:
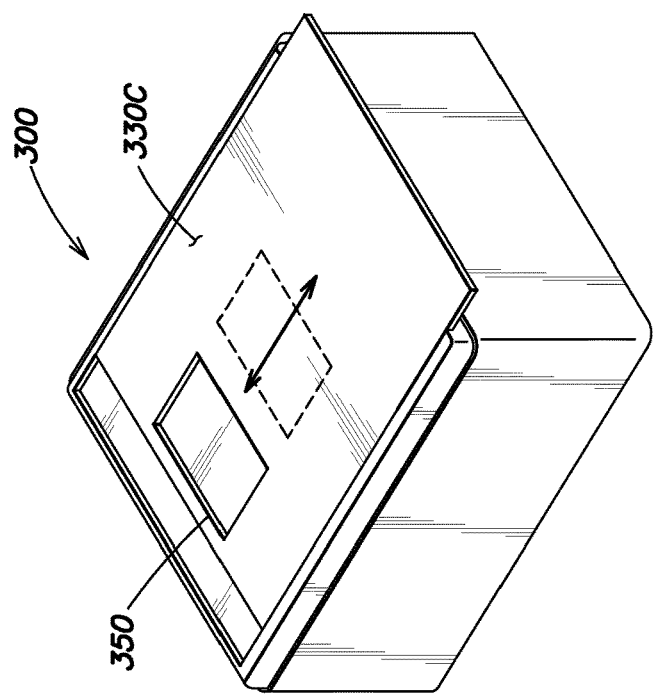
Figure 3B:
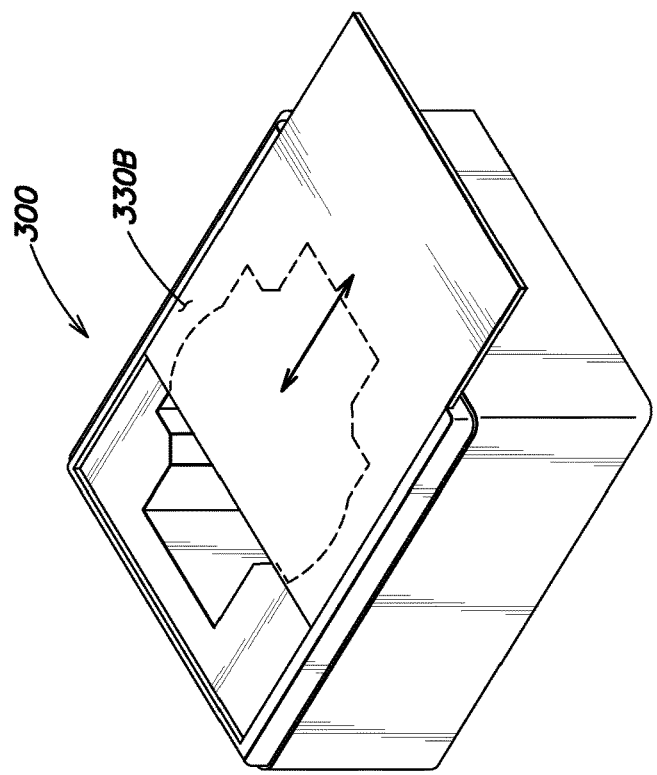

In accordance with one or more embodiments, a consumables cartridge may be inserted into a housing to facilitate trace detection of contraband. In accordance with one or more embodiments and referring to FIGS. 3A-3C, a consumables cartridge housing 300 may be constructed and arranged to receive a trace consumables cartridge. Referring to FIG. 3A, housing base 310 forms cartridge enclosure 320. A consumables cartridge (not shown) may be removably received in cartridge enclosure 320. Housing 300 may comprise lid 330A. Lid 330A may be capable of cooperating with housing base 310 to enclose cartridge enclosure 320. Lid 330A may be constructed of translucent material to allow an operator to visually identify the type of consumables and consumables cartridge in the housing without having to displace lid 330A. The translucent material may be clear or colored. Though the material may allow an operator to see through the translucent lid, the translucent material may be capable of preventing the degradation that may occur when consumables are over exposed to light.

Housing 300 may reduce the likelihood that consumables contained in the trace consumables cartridge become contaminated, spoiled, or otherwise degraded. The housing may, for instance, include a self closing lid that minimizes the exposure of the trace consumables cartridge and contained consumables to surroundings. Once an operator opens the housing lid and removes a consumable from the cartridge, an automatic closing feature may engage to close the lid. Referring to FIG. 3A, the automatic closing feature may involve a spring 340. Spring 340 may communicate with lid 330A and housing base 310. Spring 340 may cause lid 330 to automatically close opened lid 330A. Still, other features such as a weight mechanism or magnet mechanism may facilitate automatic closing of a housing lid.

In some embodiments, a re-sealable cover capable of enclosing and sealing the cavity may move. For example and referring FIG. 3A, lid 330A may move from the horizontal, sealed position, to the vertical, open position. In other embodiments and referring to FIG. 3B, a re-sealable cover 330B may move along the horizontal plane of a consumables housing base such that the cover can be displaced. In accordance with one or more embodiments, cover 330B may be displaced to a degree that allows access to the cartridge enclosure, and thus consumables loaded in a cartridge received by the cartridge enclosure. After an operator removes a selected consumable, the cover may automatically return to its undisplaced position to re-seal the cartridge enclosure. Still, in other embodiments and referring to FIG. 3C, a re-sealable cover 330C may define an opening 350. When cover 330C is engaged, opening 350 may not interfere with the seal of the cartridge enclosure. When cover 330C is displaced, opening 350 may allow access to consumables loaded in a cartridge contained in the cartridge enclosure. After an operator removes a selected consumable, cover 330C may automatically return to its undisplaced position to re-seal and enclose the cartridge enclosure.

A housing in accordance with one or more embodiments may create a substantially air tight seal of the cartridge enclosure. A cartridge housing may include a gasket. A lid may cooperate with the gasket to create a substantially air-tight seal of the housing. This feature may advantageously prevent contaminants from contaminating the consumables, may reduce consumables exposure to light and air, and may generally prevent the undesirable degradation of the consumables.

One or more embodiments of the housing may comprise a consumables holder. A consumables holder may generally be constructed and arranged for holding or retaining a consumable. In some embodiments, the consumables holder may be a small external tray connected to the housing for the purposes of holding a consumable. In other embodiments, a consumables holder may be a clam shell that pinches a consumable between two plates connected by a hinge mechanism for the purposes of retaining the consumable. The consumables holder may hold a consumable dispensed from a trace consumables cartridge prior to trapping a sample. Alternatively, the consumables holder may hold a consumable that has already trapped a sample. Additionally, the consumables holder may hold consumables used for calibrating a trace detection device before or after the consumables have been inserted into the machine for calibration.

In accordance with one or more embodiments, the housing may advantageously secure to an external surface to prevent undesirable displacement. The displacement of consumables during sampling and other trace detection activities presents an obstacle to efficient contraband detection. Consumables can become displaced from their desired location by inadvertent contact by operators, passengers, and luggage. Displacement can result in consumables becoming out of reach of the operator. Displacement may also result in the ejection of consumables from a container, and may result in consumables contamination, spoilage, and degradation. The mounting feature in accordance with one or more embodiments may advantageously ensure that a consumables cartridge housing, and thus the cartridge and consumables, do not become displaced during contraband detection activities. The mounting feature of one or more non-limiting embodiments may involve a suction cup, a magnet, hook-and-loop fasteners, or adhesive. Other mounting features will be readily identified and selected by those having skill in the art. In some embodiments, the mounting feature may be selected based on the surface to which the housing is desired to be fixed.

Figure 4C:
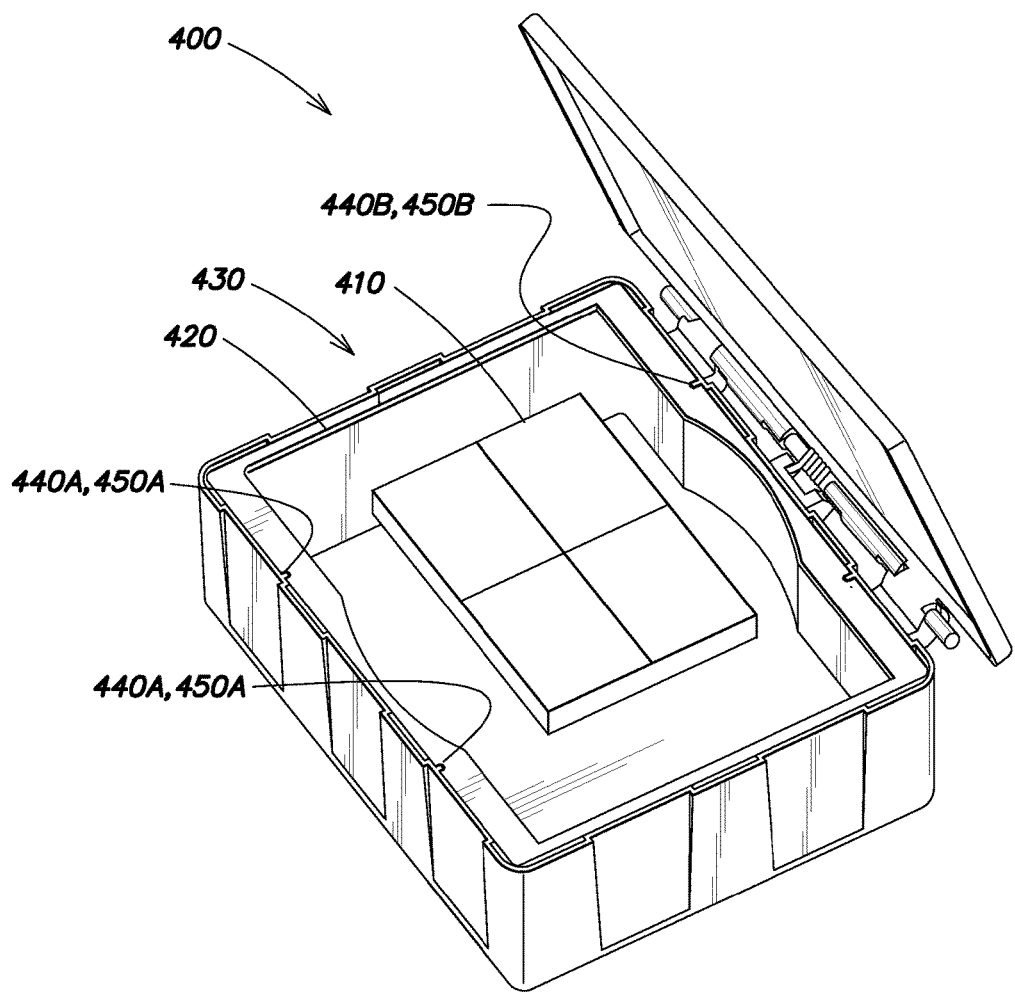
FIG. 4C presents a kit in an assembled state in accordance with one or more embodiments.

In accordance with one or more embodiments, a trace detection kit is provided to facilitate security operations. A trace detection kit may advantageously facilitate contraband detection by preserving and protecting consumables and increasing the ease with which detection activities may be carried out. In accordance with one or more embodiments and referring to FIGS. 4A and 4C, a trace detection kit may 400 include consumables 410, a consumables cartridge 420 constructed to hold consumables 410, and a cartridge housing 430 constructed to receive the consumables cartridge 420. The consumables may be pre-loaded in the cartridge. The cartridge may accommodate one type or a variety of different types of consumables. The cartridge may comprise protective features to ensure that the consumables do not become contaminated, spoiled, or otherwise degraded. The cartridge or housing may further include a dispensing mechanism for dispensing consumables. The dispensing mechanism may be a spring-loaded device that pushes consumables up and/or out of cartridge cavity to facilitate dispensing. The dispensing mechanism may also protect the consumables. The dispensing mechanism may be configured to provide an operator access to a consumable while protecting the remaining, undispensed, consumables. The dispenser may also advantageously assist an operator in procuring a desired consumable from the consumables cartridge. The cartridge containing consumables is received by the housing. The cartridge may advantageously cooperate with the housing by way of a mating feature. The mating feature may lock the consumables cartridge into place in the housing.

Aspects and embodiments of the consumables cartridge housing of a trace detection kit may prevent or reduce contamination, spoilage, or degradation of consumables. The housing may comprise a self closing lid. The lid may further cooperate with a gasket to form a substantially air tight seal of the housing. The housing may comprise additional features to further facilitate trace detection. The housing may, for example, comprise a consumables holder. The consumables holder may hold a dispensed consumable before use, after a sample is trapped and prior to insertion into a trace detection device, or at any other point in trace detection. The holder may improve the ease with which an operator performs trace detection activities.

The consumables cartridge holder may comprise an external securing mechanism that secures the housing to an external surface. Thus, when a consumables cartridge is loaded into the housing and trace detection is carried out by an operator, the trace detection kit remains securely in place. The securing mechanism prevents inadvertent movement of the kit and ensures an operator has access to consumables.

In accordance with one or more embodiments, a coding system may facilitate consumable use. Consumables, cartridges and/or housings may involve a coding system, for example, one based on color, shape or symbol, to facilitate identification of consumables by an operator as calibration consumables, verification consumables or sample consumables. Consumables housings may comprise translucent lids to further facilitate the identification of the cartridge and/or consumables in the housing. Cartridge housings may then be dedicated to a specific type of cartridge and/or consumable so that refills of like kind are used to avoid contamination. For example, a housing may be dedicated to calibration cartridges and calibration consumables or to a certain type of sample cartridge and consumables. In other embodiments, a housing may contain a plurality of cartridges and/or consumables to test for an array of contraband thus serving as a comprehensive test kit. Such housing may or may not also include calibration consumables.

In accordance with one or more embodiments, consumable use may be facilitated by providing one or more components of a trace detection kit. In some embodiments, one or more trace detection media cartridges may be provided, such as a calibration cartridge or a sample cartridge. The cartridges may be prefilled by a manufacturer of consumables. Housings for cartridges may also be provided along with instructions for storing the cartridges in the housing and for proper dispensing to prevent contamination and/or spoilage. Empty cartridges may be disposed of or recycled. Refill cartridges may be placed into the housing by the operator. In use, an operator may secure one or more housings in a working environment. For example, an operator may have a first housing for calibration cartridges and a second housing for sample cartridges. The kit may comprise a dispensing mechanism. The dispensing mechanism may be spring loaded such that a consumable is pushed up and/or out of the cartridge cavity to facilitate dispensing. The operator may first dispense a calibration consumable to test the equipment, and may then dispense a sample consumable with which to collect a sample for processing in the equipment.

It is to be appreciated that embodiments of the apparatus and methods discussed herein are not limited in application to the details of construction and the arrangement of components as set forth in the above description or illustrated in the accompanying drawings. The methods and apparatus are capable of implementation in other embodiments and of being practiced or of being carried out in various ways. Examples of specific implementations are provided herein for illustrative purposes only and are not intended to be limiting. In particular, acts, elements and features discussed in connection with any one or more embodiments are not intended to be excluded from a similar role in any other embodiment.

Also, the phraseology and terminology used herein is for the purpose of description and should not be regarded as limiting. Any references to embodiments or elements or acts of the apparatus and methods herein referred to in the singular may also embrace embodiments including a plurality of these elements, and any references in plural to any embodiment or element or act herein may also embrace embodiments including only a single element. The use herein of "including," "comprising," "having," "containing," "involving," and variations thereof is meant to encompass the items listed thereafter and equivalents thereof as well as additional items. Any references to positional or spatial orientation are intended for convenience of description, not to limit the present apparatus and methods or their components.

Having described above several aspects of at least one embodiment, it is to be appreciated that various alterations, modifications, and improvements will readily occur to those skilled in the art. Such alterations, modifications, and improvements are intended to be part of this disclosure and are intended to be within the scope of the invention. Accordingly, the foregoing description and drawings are by way of example only.

What is claimed is:

1. A consumables kit, comprising:
   a cartridge configured to receive trace detection media swabs;
   at least one trace detection media swab within the cartridge, the at least one trace detection media swab being formed from a sheet of a substrate material selected from the group consisting of paper, polyimide, polyamide, polytetrafluoroethylene, polyester, and fiberglass;
   a dispenser; and
   a cartridge housing constructed and arranged to receive the cartridge wherein the cartridge is configured to mate with the cartridge housing.

2. The kit of claim 1, wherein the cartridge includes depressions and the cartridge housing includes protrusions.

3. The kit of claim 2, wherein the depressions cooperate with the protrusions to mate the cartridge within the cartridge housing.

4. A consumables kit, comprising:
   a cartridge configured to receive trace detection media swabs;
   at least one trace detection media swab within the cartridge, the at least one trace detection media swab being formed from a sheet of a substrate material selected from the group consisting of paper, polyimide, polyamide, polytetrafluoroethylene, polyester, and fiberglass;
   a dispenser; and
   a cartridge housing constructed and arranged to receive the cartridge,
   wherein the housing comprises a self-closing lid, and wherein the lid is translucent.

5. A consumables kit, comprising:
   a cartridge configured to receive trace detection media swabs;
   at least one trace detection media swab within the cartridge, the at least one trace detection media swab being formed from a sheet of a substrate material selected from the group consisting of paper, polyimide, polyamide, polytetrafluoroethylene, polyester, and fiberglass;
   a dispenser; and
   a cartridge housing constructed and arranged to receive the cartridge, wherein the cartridge is constructed and arranged to hold trace detection media swabs having a plurality of geometries.

6. The kit of claim 5, wherein the cartridge includes a cavity constructed and arranged to hold trace detection media swabs having a plurality of geometries.

* * * * *